United States Patent [19]
Chihani et al.

[11] Patent Number: 5,885,266
[45] Date of Patent: Mar. 23, 1999

[54] ABSORBENT ARTICLE SUCH AS A DIAPER, AN INCONTINENCE GUARD, A SANITARY NAPKIN OR LIKE ARTICLE

[75] Inventors: Thami Chihani; Anders Silfverstrand, both of Mölnlycke, Sweden

[73] Assignee: SCA Molnlycke AB, Gothenburg, Sweden

[21] Appl. No.: 809,235

[22] PCT Filed: Sep. 27, 1995

[86] PCT No.: PCT/SE95/01100

§ 371 Date: Mar. 19, 1997

§ 102(e) Date: Mar. 19, 1997

[87] PCT Pub. No.: WO96/13283

PCT Pub. Date: May 9, 1996

[30] Foreign Application Priority Data

Oct. 27, 1994 [SE] Sweden ................................ 9403689

[51] Int. Cl.$^6$ ................................. A61F 13/15; C09J 4/00
[52] U.S. Cl. .......................... 604/378; 604/367; 156/325; 156/328; 156/332; 156/308.4
[58] Field of Search ...................................... 604/367, 368, 604/378; 526/935; 156/325, 328, 332, 308.4, 73.1

[56] References Cited

U.S. PATENT DOCUMENTS 5,356,405 10/1994 Thompson et al. .
5,356,963 10/1994 Kauffman et al. .

*Primary Examiner*—Robert A. Clarke
*Attorney, Agent, or Firm*—Young & Thompson

[57] ABSTRACT

An absorbent article such as a diaper, an incontinence guard or a sanitary napkin includes a liquid-permeable outer sheet, a liquid-impermeable bottom sheet and an absorbent body placed therebetween. The outer sheet and the absorbent body are at least partially joined together with a hydrophilic glue.

21 Claims, 7 Drawing Sheets

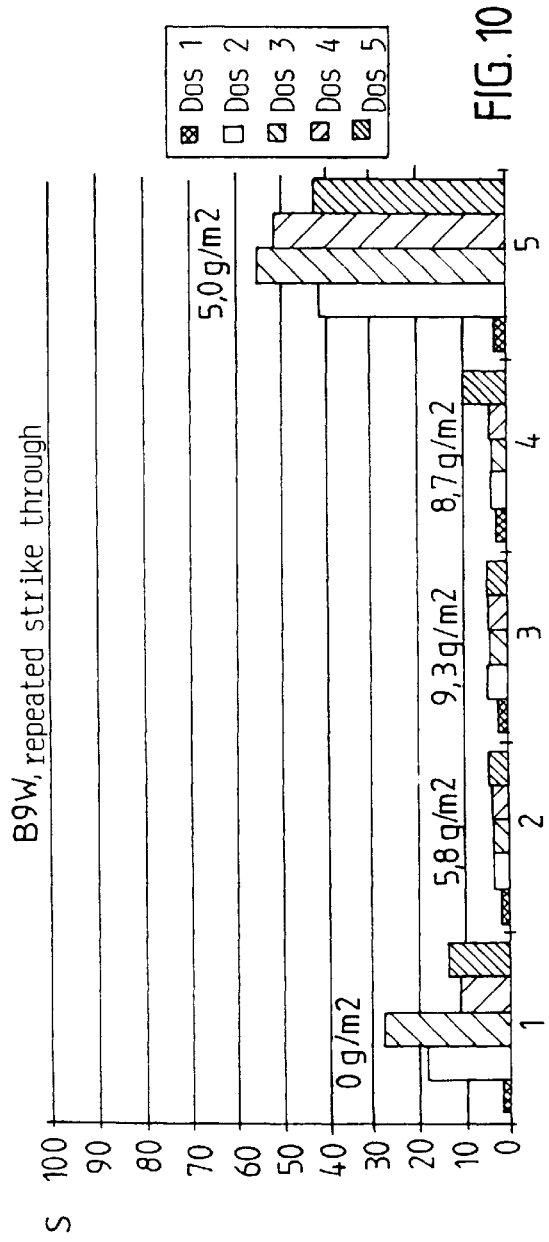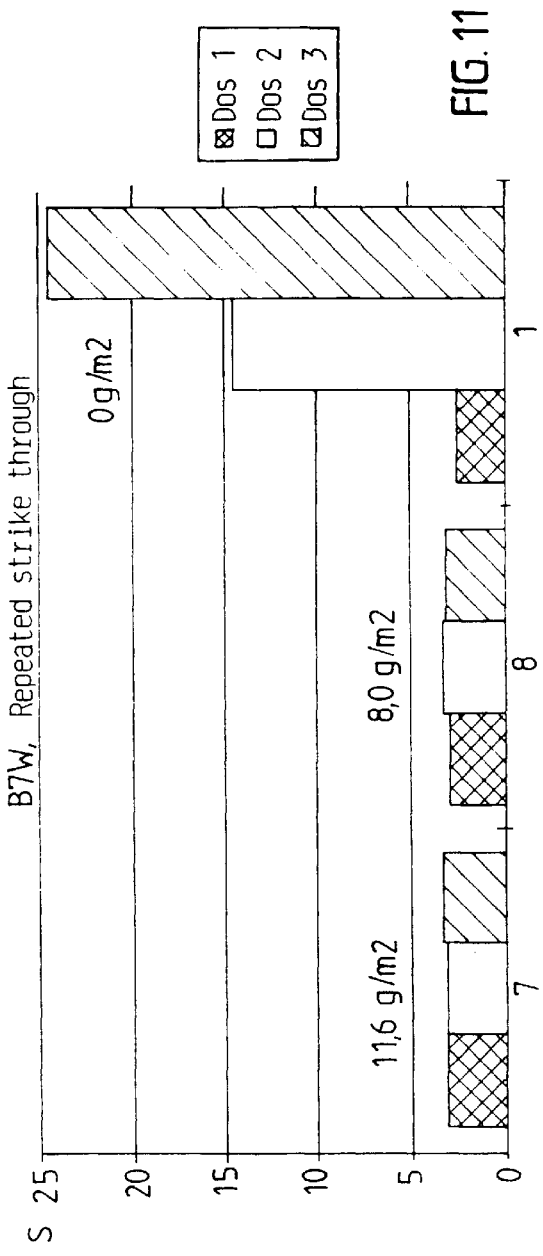

ABSORBENT ARTICLE SUCH AS A DIAPER, AN INCONTINENCE GUARD, A SANITARY NAPKIN OR LIKE ARTICLE

CROSS REFERENCE TO RELATED APPLICATIONS

This application is the 35 USC 371 national stage of International application PCT/SE95/01100 filed on Sep. 27, 1995, which designates the United States of America.

FIELD OF THE INVENTION

The present invention relates to an absorbent article such as a diaper, an incontinence guard or a sanitary napkin, and also to the use of a hydrophilic glue in the manufacture of an absorbent article.

BACKGROUND OF THE INVENTION

Hydrophilic glues are previously known from EP-A 1,297,769 for instance. This document describes a hydrophilic glue composition which can be used conveniently in products that are to be fastened to the skin, such as bandages.

U.S. Pat. No. 4,785,030 teaches a latex composition which when the liquid phase is removed, forms a film whose surface is hydrophilic. The latex composition can be used as a glue for fabric-like paper products.

U.S. Pat. No. 5,356,405 discloses adsorbent articles with a fast liquid transport through the outer layers to an absorbent body. This is achieved by arranging capillary channel fibres between the outer sheet and the absorbent body.

U.S. Pat. No. 5,356,963 describes hydrophilic hot melt adhesives for use in remoistenable applications. The document briefly mentions that the adhesives can be used in envelopes, bag sealing, bookbinding, diapers etc. without giving any construction details.

A surface sheet of an absorbent article, such as a diaper, an incontinence guard or a sanitary napkin, is normally comprised of nonwoven material, which is usually hydrophobic. In order to enable fluid, such as urine or menstruation fluid, to pass through this outer layer, the nonwoven layer is treated with a surfactant in order to make it hydrophilic. In order for a material to be considered to be hydrophilic, it must have a wetting angle of less than 90°. Repeated wetting of the material will wash out the surfactant and the surface material will then become hydrophobic. This makes it difficult for liquid to pass down through the surface layer.

OBJECTS OF THE INVENTION

The outer sheet is usually attached to the absorbent body by means of a hot melt glue. This glue is hydrophobic. One object of the present invention is to solve the problem of surfactants being washed out of the outer sheet and therewith prevent liquid from passing therethrough. It has surprisingly been found that this problem can be solved by joining the outer sheet to the absorbent body with a hydrophilic glue, such as to retain a hydrophilic surface which will continue to allow liquid to pass therethrough, despite being wetted repeatedly.

Another object of the present invention is to avoid the hydrophobic barrier that is formed by hydrophobic hot melt glues in present-day absorbent products.

A typical problem with absorbent articles is that the outer sheet loosens from the absorbent body after being wetted only once. In such cases, the hydrophilic glue is the bridging link which makes continued liquid transport possible.

SUMMARY OF THE INVENTION

According to the present invention, there may be used either a hydrophilic glue, for instance a dispersion glue, or a hydrophobic glue, for instance a hot melt, which has been made hydrophilic by modification. One advantage with using a modified hot melt is that it avoids a vapourization stage of the water in the dispersion glue, in the process of manufacturing the absorbent article. The hot melt can be modified by grafting an otherwise hydrophobic polymer, or by adding a surfactant to an otherwise hydrophobic hot melt, or by using starch as the base in the hot melt.

A hot melt glue which is based on a grafted polymer will preferably include 75–85 percent by weight of a graft copolymer and 15–25 percent by weight of an adhesive agent. The graft copolymer consists in 40–80 percent by weight of a vinyl monomer and 20–60 percent by weight of a water-soluble polyalkene oxide. The vinyl monomer is preferably vinyl acetate or an alkyl substituted acrylate, such as methyl acrylate or ethyl acrylate. The polyalkene oxide is preferably selected from the group including homopolymers of ethene oxide, copolymers of ethene oxide and propene oxide, and mixtures thereof. The adhesive agent may be a synthetic or natural resin.

A hot melt which has been made hydrophilic by adding a surfactant may be based on a thermoplastic elastomer or an atactic poly-α-olefin, as atactic polypropylene. The surfactant added is preferably non-ionic. The non-ionic surfactant may be an alcohol, an alkanolamide, an amino oxide, an ester or an ether.

A starch-based hydrophilic hot melt includes a modified starch ester. The ester may be based on natural starch, for instance from maize, potato, wheat, rice, or on a synthetically produced starch. Examples of modified starch are starch propionate and starch acetate. In addition to containing the starch ester, the hot melt also includes an organic solvent which imparts the properties of a hot melt glue to the composition. The solvent may, for instance, be a sulfonamide, a carboxylic acid, a carboxylic acid ester, an amide, a phosphate ester, an alcohol or an ester. The solvent will preferably be a sulfonamide, an alcohol, an amide or an ester.

The hydrophilic glue can be applied to the surface of a nonwoven sheet that has been pretreated with a surfactant. This will result in a more permanent hydrophilic surface than that which would be obtained by treating the nonwoven sheet solely with a surfactant. The hydrophilic glue may also be used on a hydrophobic nonwoven material that has not been pretreated with surfactants. In this case, the hydrophilic glue has the important function of penetrating into the nonwoven material and reducing resistance to the transportation of liquid, this resistance being relatively high in the case of thick nonwoven materials.

The hydrophilic glue can be applied in different ways. The glue can be spread over the whole of the surface to be joined. Moreover, the hydrophilic glue can be applied solely in the wetting area. The wetting area is the area on the absorbent body which initially receives the liquid, or fluid, discharged by the wearer. As will be understood, the wetting area will be located in different places, depending on the type of article concerned and also on the sex of the wearer. The remaining surface to be joined can be glued with a hydrophobic glue, such as a conventional hot melt glue. The advantage with this method is that rewetting is prevented in those parts that are covered with the hydrophobic glue. Another gluing method which will prevent rewetting involves distributing the hydrophilic glue in a pattern, such as a strip pattern, a checkered pattern or a punctiform pattern, over the surface to be glued. The material lying between the glue pattern will thus be hydrophobic and prevent rewetting. The glue strips may extend either longitudinally or transversely on the article concerned.

The glue may be applied, for instance, by spraying, complete coating or screen-printing techniques.

The absorbent body includes conventional absorbent material, for instance cellulose fibres, viscose fibres or superabsorbent synthetic polymers, such as polyacrylates. The use of mixtures of different absorbent materials is also conceivable, of course.

The outer sheet comprised of a nonwoven material. This may be a conventional nonwoven, for instance a spunbonded nonwoven or a carded nonwoven. Naturally, a hydrophilic glue may also be used to glue an outer sheet that is made from plastic film. Both the outer sheet and the absorbent body may comprise more than one layer.

BRIEF DESCRIPTION OF THE DRAWINGS

The invention will now be described in more detail with reference to exemplifying embodiments thereof and also with reference to the accompanying drawings. It will be understood that the invention is not restricted to the described and illustrated exemplifying embodiments thereof since these embodiments are merely intended to explain and illustrate the invention.

FIGS. 10 and 11 show the results obtained with repeated strike through tests on nonwoven which had been pretreated with a surfactant.

DETAILED DESCRIPTION OF THE INVENTION

The invention will be further described with reference to the following examples.

EXAMPLE 1

Determining run-off tests on nonwoven

Principle

Measuring the amount of liquid that remains unabsorbed when a known quantity of test liquid is poured onto nonwoven/filter paper placed on a sloping surface. Run-off is measured three times in succession on one and the same nonwoven sample, although the filter paper is changed between each measuring occasion.

Equipment

Figure 1A:
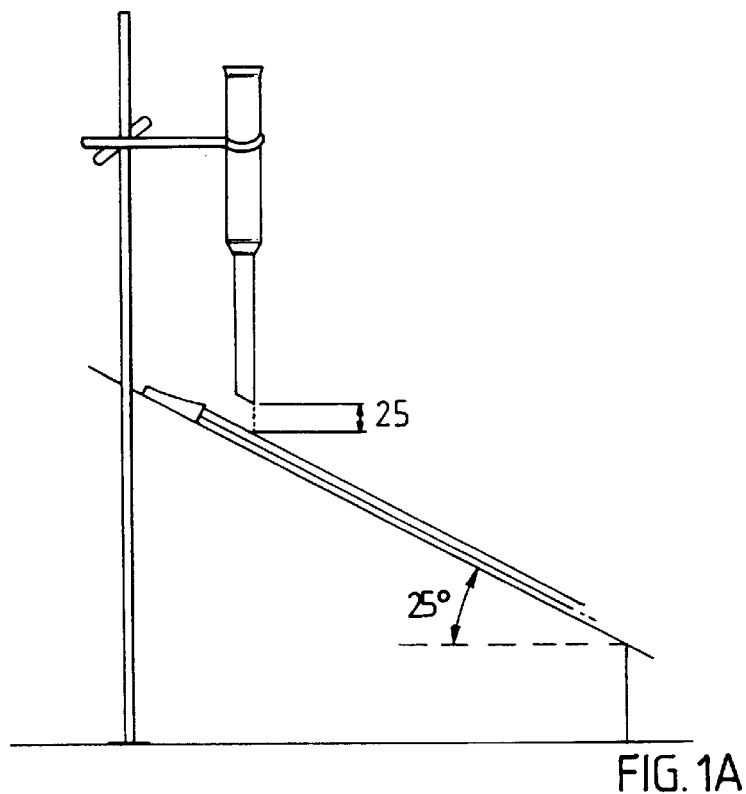
FIG. 1 illustrates an experimental run-off test.
Figure 1:
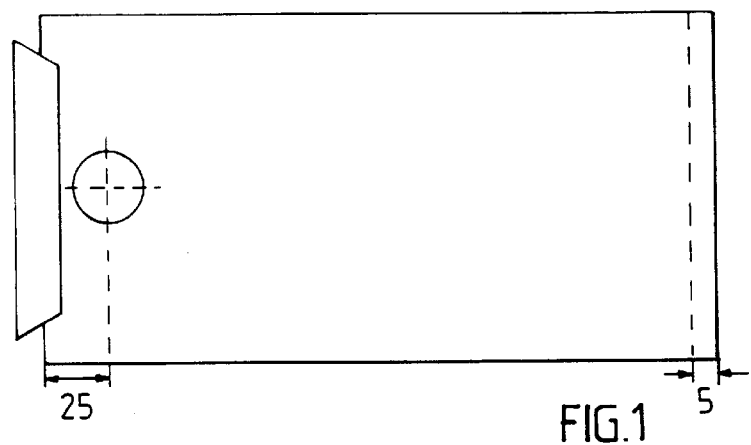

Measuring table with adjustable table inclination; see FIG. 1.

Stand.

Metering pump connected to hose and outlet pipe or burette.

Filter paper FF3 W/S (Hollingworth & Vose Co. Ltd.), 140×280 mm, long side in the machine direction.

Absorbent paper.

Test liquid, 0.9% NaCl solution produced with deionized water.

Sample preparation

Nonwoven samples were cut-out, 140×285 mm, with the long side in the length direction. The measuring table was inclined at an angle of 25°. The distance between the outlet orifice of the outlet pipe and the sample was adjusted to 25 mm. The metering pump was set to meter a quantity, or dosage, of 25 ml at a metering rate of 7 ml/s. The absorbent paper was weighed to an accuracy of 0.01 g.

Procedure

Two filter papers were placed on the inclined surface with the smooth sides facing upwards. The nonwoven paper was placed on top of the filter papers with a 5 mm overshoot at the lower edge. Filter papers and nonwoven were secured with a metal clamp. The metering equipment was set to discharge liquid at a point 25 mm from the upper edge of the sample. Metering of the liquid was carried out. The absorbent paper with the overrun liquid was weighed. The wet filter papers were removed after a waiting time of four minutes and the same nonwoven sample was placed on two fresh filter papers. The run-off test was repeated a further four times using 25 ml of test liquid on each metering occasion.

Run-Off tests were carried out with the following materials

Glue:

1) No glue applied.
2) Hydrophilic dispersion glue based on polyvinyl acetate, stabilized with polyvinyl alcohol.
3) Hydrophilic dispersion glue based on an ethylene-vinyl acetate copolymer.
4) Hydrophilic dispersion glue based on a partially cross-linked ethylene-vinyl acetate copolymer.
5) Hydrophobic hot melt based on an atactic poly-α-olefin.
6) Hydrophobic hot melt based on a starch ester.
7) Hydrophobic hot melt based on a graft copolymer of vinyl acetate and polyethylene oxide.
8) Hydrophobic hot melt based on atactic polypropylene and an non-ionic surfactant.

Nonwoven:

Holmestra B9W (Fiber Web), 20 g/m$^2$, pretreated with surfactant.

Holmestra N9W (Fiber Web), 17 g/m$^2$, not pretreated with surfactant.

Holmestra B7W (Fiber Web), 20 g/m$^2$, pretreated with surfactant.

Holmestra N7W (Fiber Web), 20 g/m$^2$, not pretreated with surfactant.

Test results

Figure 6:
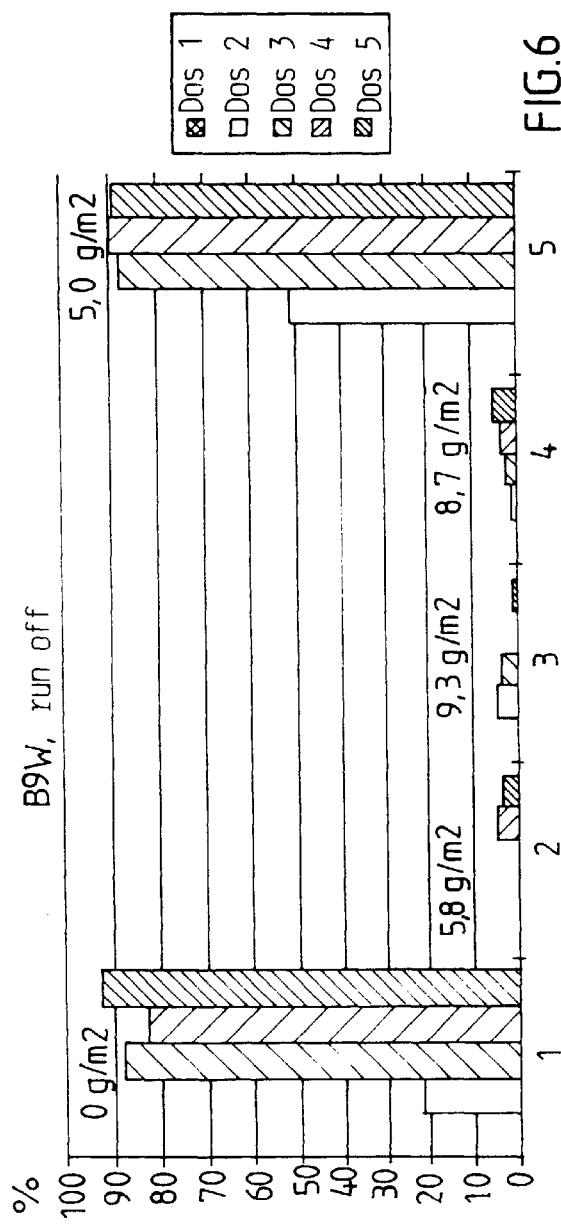
FIGS. 6 and 7 show the result of a run-off test carried out on nonwoven that had been pretreated with a surfactant.
Figure 7:
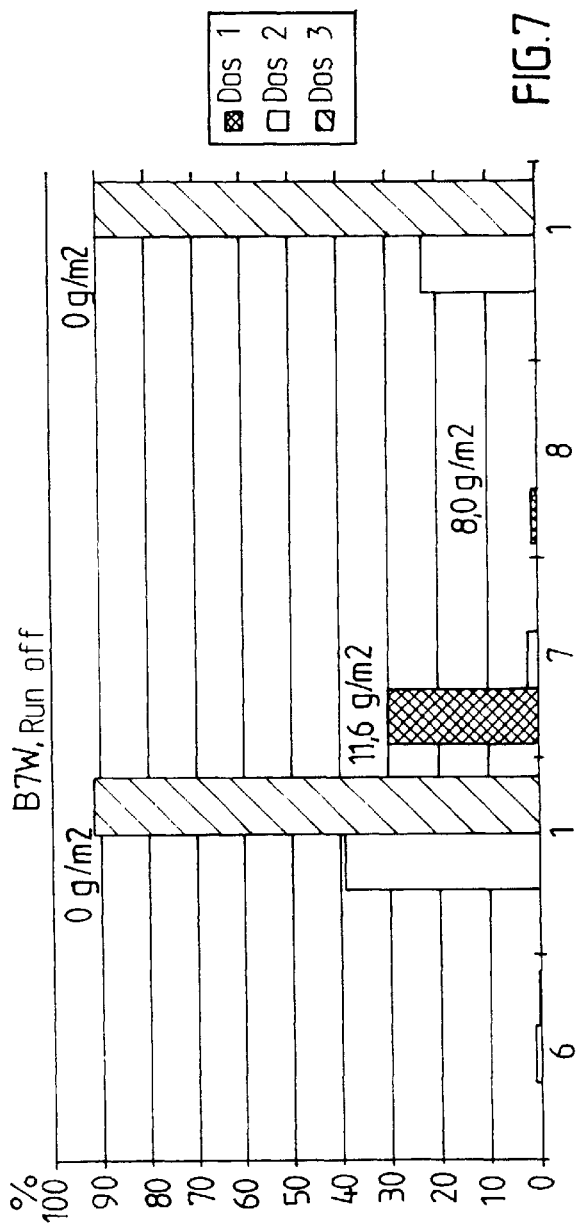
Figure 8:
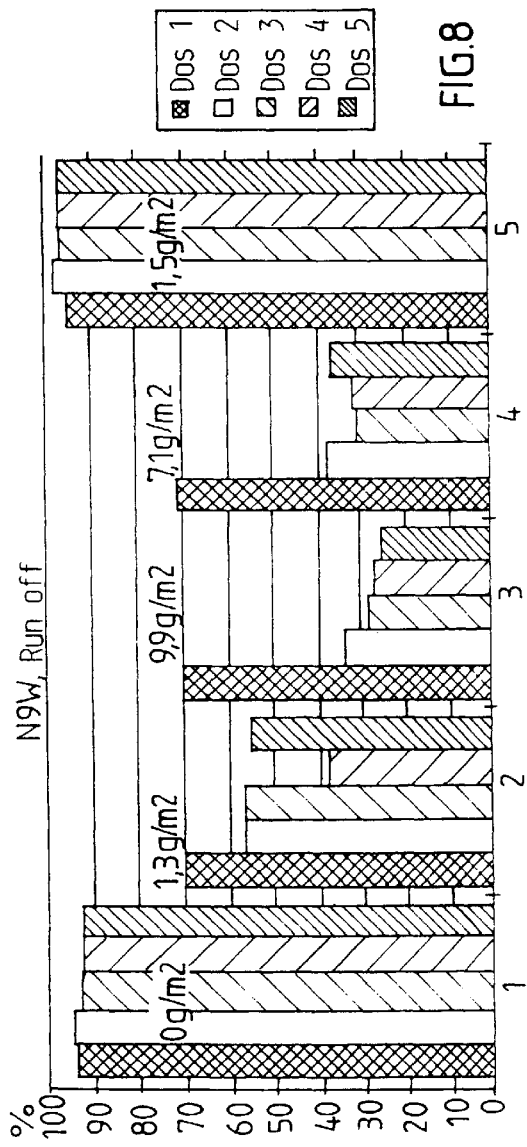
FIGS. 8 and 9 show the result of a run-off test carried out on nonwoven which had not been pretreated with a surfactant.
Figure 9:
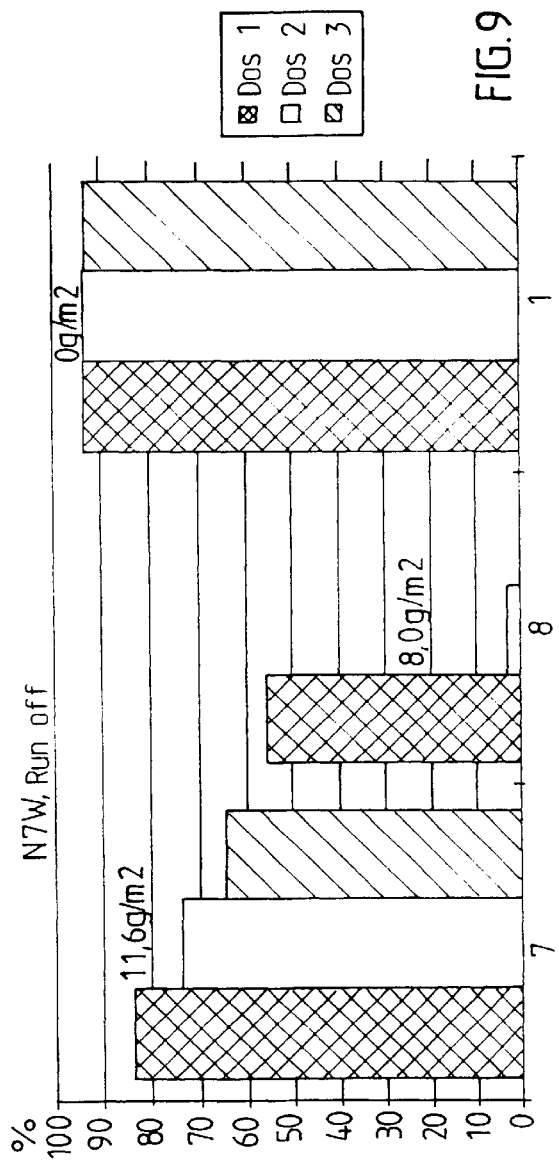

See FIGS. 6–9. These Figures show the extent to which the applied liquid runs-off. The various columns within the same groups show the results obtained with the different liquid dosages on the same nonwoven sample. The Figures above the columns denote the amount of glue that was applied. FIGS. 6–7 show the results obtained with surfactant-treated nonwoven. FIGS. 8–9 show the results obtained with nonwoven that had not been treated with a surfactant.

EXAMPLE 2

Determining repeated strike through on nonwoven.

Principle

Measuring the time required for a specific quantity of liquid (synthetic urine) to pass through a nonwoven material and thereafter be absorbed by an absorbent core. The time was measured five times in sequence on one and the same nonwoven sample, but with a change of filter paper between each measuring occasion.

Equipment

Figure 2:
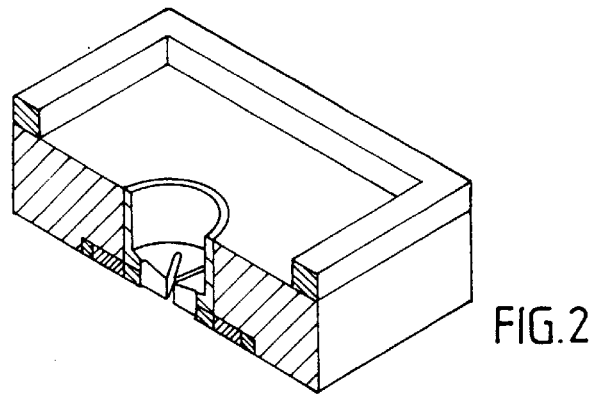
FIG. 2 illustrates a strike through plate used to determine permeability.
Figure 3:
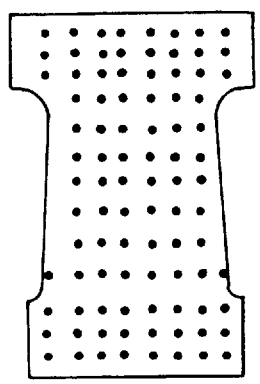
FIG. 3 illustrates an example of how the hydrophilic glue can be applied to a diaper in a punctiform pattern.
Figure 4:
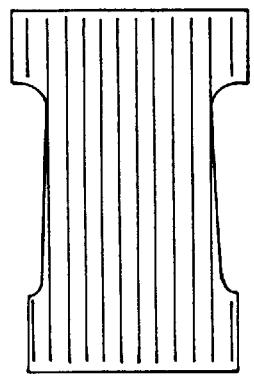
FIG. 4 illustrates an example of how the hydrophilic glue can be applied to a diaper in a strip pattern.
Figure 5:
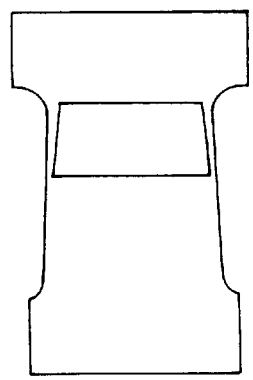
FIG. 5 illustrates an example of how the glue can be applied at the wetting area of a diaper.

Strike through plate (see FIG. 2) and instruments for measuring the strike through time: LISTER Lenzing AG.

Plexiglass bottom plate, 125×125 mm.

Timer, accurate to 0.1 s.

Measuring cylinders: 5 and 50 ml or digital burette.

Absorbent core: FF3 W/S filter paper 100×200 mm (Hollingworth & Vose Co. Ltd.).

Synthetic urine, 9 g NaCl/1000 ml distilled water.

Laboratory scales, accurate to 0.01 g.

Sample preparation

Samples measuring 125×125 mm were clipped from the test material. Samples and filter paper were conditioned in 65% atmospheric humidity for four hours at 20° C.

Procedure

Five layers of filter paper were placed on the bottom plate with their smooth sides facing upwards. A nonwoven sample was placed on top of the filter papers. The strike through plate was placed on top of the sample, well centred in relation thereto. The instrument was adjusted vertically so that the distance between the outlet orifice of the outlet pipe and the upper part of the plate was 5 mm, in other words 30 mm above the sample. 5 ml synthetic urine were measured-up and poured into the liquid container of the measuring instrument. Metering of the liquid was commenced and the strike through time was noted to an accuracy of 0.1 s. The timer was started and the strike through plate was removed after a period of four minutes. The wet filter papers were removed. The same nonwoven sample was placed on five fresh filter papers. The strike through, or through-wetting, procedure was repeated two more times.

A permeability test was carried out with the following materials

Glue:

1) No glue applied.
2) Hydrophilic dispersion glue based on polyvinyl acetate, stabilized with polyvinyl alcohol.
3) Hydrophilic dispersion glue based on an ethylene-vinyl acetate copolymer.
4) Hydrophilic dispersion glue based on a partially cross-linked ethylene-vinyl acetate copolymer.
5) Hydrophobic hot melt based on an atactic poly-α-olefin.
6) Hydrophobic hot melt based on a starch ester.
7) Hydrophobic hot melt based on a graft copolymer of vinyl acetate and polyethylene oxide.
8) Hydrophobic hot melt based on atactic polypropylene and an non-ionic surfactant.

Nonwoven:

Holmestra B9W (Fiber Web), 20 g/m$^2$, pretreated with surfactant.

Holmestra N9W (Fiber Web), 17 g/m$^2$, not pretreated with surfactant.

Holmestra B7W (Fiber Web), 20 g/m$^2$, pretreated with surfactant.

Holmestra N7W (Fiber Web), 20 g/m$^2$, not pretreated with surfactant.

Test results

Figure 12:
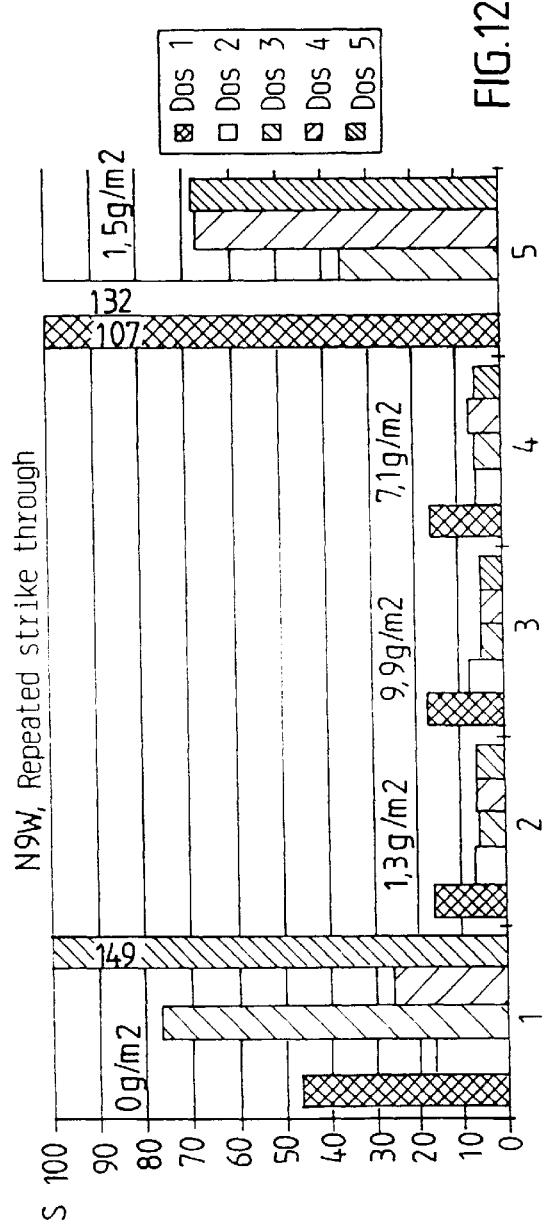
FIGS. 12 and 13 show the results obtained with repeated strike through tests on nonwoven which had not been pretreated with a surfactant.
Figure 13:
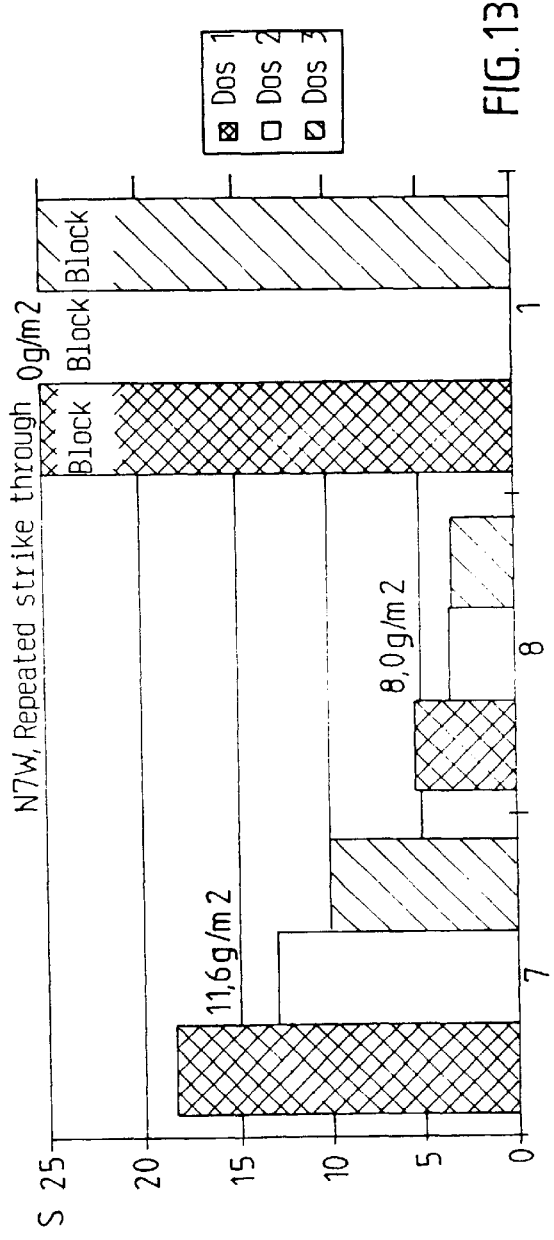
Figure 14:
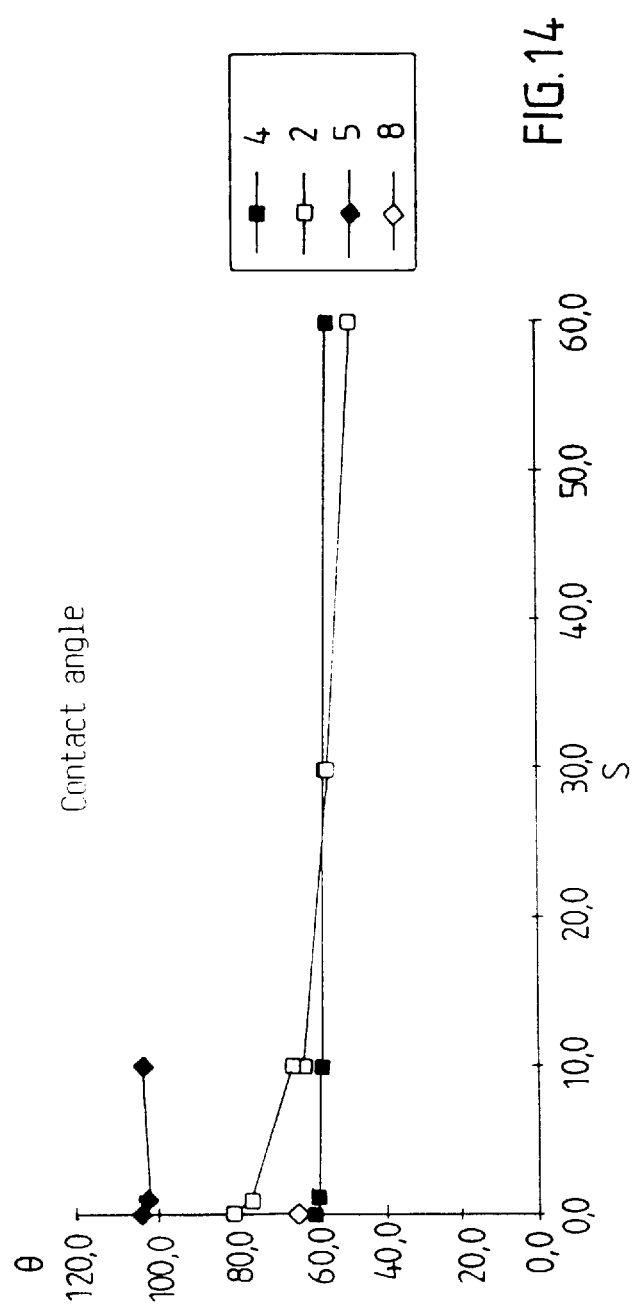
FIG. 14 illustrates the results obtained when measuring the glue contact angles.

See FIGS. 10–13. The various columns within the same group show the results obtained when metering liquid onto the same nonwoven sample with different dosages. The Figures above the columns denote the amount of glue applied. FIGS. 10–11 show the results obtained with the surfactant-treated nonwoven. FIGS. 12–13 show the results obtained with the nonwoven that was not treated with surfactant.

EXAMPLE 3

Measuring the glue contact angle

Principle

In order for a glue to be considered hydrophilic, the contact angle θ between a water droplet and the material to be measured shall be smaller than 90°.

Equipment

The contact angle was measured on a DAT (dynamic absorption tester).

Distilled water.

Paper, surface weight 80 g/m$^2$.

Procedure

Three different glues were applied to paper. Strips measuring 25 mm in width were then cut from the sample. Two different tests were carried out: one test involving measuring at 0.1, 1.0 and 10.0 seconds and another test involving measuring at 10.0, 30.0 and 60.0 seconds. Measurements were carried out only at 0.1, 1.0 and 10.0 seconds on sample 5). Measurements were carried out only at 0.1 second on sample 8).

Contact angle measurements were made on the following glues

2) Hydrophilic dispersion glue based on polyvinyl acetate stabilized with polyvinyl alcohol.
4) Hydrophilic dispersion glue based on a partially-cross-link ethylene-vinyl acetate copolymer.
5) Hydrophobic hot melt based on an atactic poly-α-olefin. Hydrophobic hot melt based on an atactic poly-α-olefin.
8) Hydrophobic hot melt based on atactic polypropylene and a non-ionic surfactant.

Test results

See FIG. 11.

What is claimed is:

1. A method of making an absorbent article selected from the group consisting of a diaper, an incontinence guard and a sanitary napkin which comprises a liquid-permeable outer sheet, a liquid-impermeable backing sheet, and an absorbent body placed therebetween, the method comprising joining the outer sheet directly to the absorbent body with a hydrophilic glue, thereby to reduce the resistance to the transportation of liquid.

2. The method according to claim 1, wherein the outer sheet and the absorbent body are mutually joined by a continuous layer of hydrophilic glue.

3. The method according to claim 1, wherein the outer sheet and the absorbent body are mutually joined by a hydrophilic glue distributed in a pattern.

4. The method according to claim 3, wherein the pattern is a punctiform pattern.

5. The method according to claim 3, wherein the pattern is a striped pattern or a squared pattern.

6. The method according to claim 1, wherein the hydrophilic glue is applied solely at the wetting area.

7. The method according to claim 1, wherein the hydrophilic glue is an originally hydrophobic glue which has been modified to become hydrophilic.

8. The method according to claim 1, wherein the hydrophilic glue is a dispersion glue.

9. The method according to claim 7, wherein the hydrophobic glue is a hot melt glue that has been modified by adding a surfactant.

10. The method according to claim 7, wherein the hydrophobic glue has been modified by grafting a hydrophilic group on an otherwise hydrophobic polymer.

11. The method according to claim 7, wherein the hydrophilic glue is a starch-based hot-melt glue.

12. An absorbent article selected from the group consisting of a diaper, an incontinence guard and a sanitary napkin said absorbent article comprising a liquid-permeable outer sheet, a liquid-impermeable backing sheet, and an absorbent body placed therebetween, wherein the outer sheet and the absorbent body, at least partially, are mutually and directly joined by a hydrophilic hot melt glue applied at the wetting area.

13. The absorbent article according to claim 12, wherein the hydrophilic glue is an originally hydrophobic glue which has been modified to become hydrophilic.

14. The absorbent article according to claim 13, wherein the hydrophobic glue is a hot melt glue that has been modified by adding a surfactant.

15. The absorbent article according to claim 13, wherein the hydrophobic glue has been modified by grafting a hydrophilic group on an otherwise hydrophobic polymer.

16. The absorbent article according to claim 13, wherein the hydrophilic glue is a starch-based hot-melt glue.

17. The absorbent article according to claim 12, wherein the outer sheet and the absorbent body are mutually joined by a continous layer of hydrophilic hot melt glue.

18. The absorbent article according to claim 12, wherein the outer sheet and the absorbent body are mutually joined by a hydrophilic hot melt glue distributed in a pattern.

19. The absorbent article according to claim 18, wherein the pattern is a punctiform pattern.

20. The absorbent article according to claim 18, wherein the pattern is a striped pattern or a squared pattern.

21. The absorbent article according to claim 12, wherein the hydrophilic glue is applied solely at the wetting area.

\* \* \* \* \*